US008610092B2

(12) United States Patent
Rue et al.

(10) Patent No.: US 8,610,092 B2
(45) Date of Patent: Dec. 17, 2013

(54) CHARGED PARTICLE BEAM PROCESSING SYSTEM WITH VISUAL AND INFRARED IMAGING

(75) Inventors: Chad Rue, Portland, OR (US); Enrique Agorio, Lake Oswego, OR (US); Daniel Crowley, legal representative, San Mateo, CA (US)

(73) Assignee: FEI Company, Hillsboro, OR (US)

( * ) Notice: Subject to any disclaimer, the term of this patent is extended or adjusted under 35 U.S.C. 154(b) by 81 days.

(21) Appl. No.: 13/179,109

(22) Filed: Jul. 8, 2011

(65) Prior Publication Data
US 2012/0006987 A1 Jan. 12, 2012

Related U.S. Application Data

(60) Provisional application No. 61/362,381, filed on Jul. 8, 2010.

(51) Int. Cl.
*A61N 5/10* (2006.01)
(52) U.S. Cl.
USPC ........................................ 250/492.3
(58) Field of Classification Search
USPC .......................... 250/492.2–492.3
See application file for complete search history.

(56) References Cited

U.S. PATENT DOCUMENTS

| 5,140,164 A | 8/1992 | Talbot et al. |
| 5,216,235 A | 6/1993 | Lin |
| 5,821,549 A * | 10/1998 | Talbot et al. ............ 850/62 |
| 5,976,328 A | 11/1999 | Azuma et al. |
| 6,373,070 B1 * | 4/2002 | Rasmussen ............ 250/492.21 |
| 7,015,485 B2 * | 3/2006 | Kitagawa ............ 250/458.1 |
| 7,135,123 B1 * | 11/2006 | Thompson et al. ............ 216/59 |
| 7,718,979 B2 | 5/2010 | Knowles |
| 2003/0102436 A1 | 6/2003 | Benas-Sayag et al. |
| 2004/0245453 A1 | 12/2004 | Izgarian et al. |
| 2008/0067369 A1 * | 3/2008 | Marchman et al. ............ 250/306 |

FOREIGN PATENT DOCUMENTS

| JP | 636727 | 2/1994 |
| JP | 9205079 | 8/1997 |
| WO | 2012006558 | 1/2012 |

OTHER PUBLICATIONS

'JAI's New 2-CCD Camera,' http://www.jai.com/SiteCollectionDocuments/Camera_Solutions_Other_Documents/AD-080CL_Article.pdf, 2 pages, retrieved May 13, 2010.

* cited by examiner

*Primary Examiner* — Casey Bryant
(74) *Attorney, Agent, or Firm* — Scheinberg & Associates, PC; Michael O. Scheinberg

(57) ABSTRACT

A charged particle beam system for processing substrates is disclosed, comprising a charged particle column, combination infrared radiation and visible light illumination and imaging subsystems, in-vacuum optics, and a precision stage for supporting and positioning the substrate alternately under the charged particle column and the imaging system. The axes of the charged particle column and imaging system are offset to enable much closer working distances for both imaging and beam processing than would be possible in a single integrated assembly. A method for extremely accurately calibrating the offset between the column and imaging system is disclosed, enabling beam processing at precisely-determined locations on the substrate. The imaging system is capable of locating sub-surface features on the substrate which cannot be seen using the charged particle beam. Two illumination modes are disclosed, enabling both bright-field and dark-field imaging in infrared radiation and visible light.

16 Claims, 12 Drawing Sheets

CHARGED PARTICLE BEAM PROCESSING SYSTEM WITH VISUAL AND INFRARED IMAGING

This application claims priority from U.S. Prov. App. 61/362,381 filed Jul. 8, 2010, which is hereby incorporate by reference.

TECHNICAL FIELD OF THE INVENTION

The present invention relates to charged particle beam processing systems.

BACKGROUND OF THE INVENTION

Processing of substrates by means of focused charged particle beams is a well-established technique in a wide range of technological areas, in particular, semiconductor manufacturing. Often, it is desired to perform processing of structures on a semiconductor device, where these structures are buried beneath several microns of material (such as silicon) which is opaque to visible light. Near-infrared (NIR) imaging has an advantage of being able to penetrate through these layers, however, with reduced spatial resolution due to the longer wavelengths of NIR light. Visible light has some ability to penetrate these layers, as well.

One example of a charged particle beam process is backside circuit editing, applicable to flip-chip devices, where the only way to access internal regions of the devices in the circuit is by removing material from the back of the chip, typically with focused ion beam (FIB) milling. After a sufficient amount of material has been milled away, the circuit layers can be imaged using visible light to locate the exact device positions for charged particle beam processing, such as cutting and adding interconnects.

Another example of a charged particle beam process is front-side circuit editing. Often, the layers of interest for processing may be beneath 1-5 µm of silicon, which is largely opaque to visible light (for $\lambda<1.1$ µm, corresponding to the bandgap energy of silicon). When bright-field imaging (where the illumination is normal to the substrate surface) is attempted using visible light, there is generally too much absorption to enable imaging of these buried structures, plus, reflected light off the substrate surface interferes with light scattered from within the device, resulting in loss of image contrast. Using dark-field imaging (where the visible light illumination of the device is at a glancing angle to the substrate), imaging is possible, since the reflected light from the substrate surface does not contribute to the overall image.

Thus, there is a need for both near-infrared imaging (with superior depth penetration through silicon) and visible light imaging (with superior spatial resolution due to the shorter wavelength) for use in locating structures within semiconductor devices which are to be processed with a charged particle beam.

In some systems combining both optical imaging for navigation (i.e., locating areas for beam processing) and charged particle beam processing columns, the imaging and processing subsystems are integrated together within a small volume, where both the imaging and processing may be performed without the need for substrate motion. A generally serious limitation of these implementations is that the imaging and processing subsystems physically interfere with each other due to their respective diameters. Also, it is not possible for both imaging and processing to be perpendicular to the substrate surface. Both these disadvantages tend to limit the achievable spatial resolutions, both for imaging and for the subsequent beam processing steps. Thus, alternative system designs have been used in which the axes of the imaging subsystem and the charged particle column are separated and the substrate is moved between the two subsystems, alternatively being imaged and then processed, often over many cycles, where the imaging process serves for both initially locating regions before processing begins and then for end-point detection during processing. In these implementations with physically separated imaging and processing subsystems, it is obviously necessary to know the separation of these two subsystems very precisely.

Structures near or at the surface of a substrate, such as a microcircuit, may not be easily imaged using the charged particle beam. The difficulty in charged particle beam imaging may arise due to lack of sufficient image contrast, or due to the fact that the charged particle beam may induce damage, such as milling or contamination, as a result of the imaging process. Thus, it is useful to have an imaging process that does not damage the substrate prior to processing. In some charged particle beam processing systems, an optical imaging capability is integrated into the same physical region of the system as the charged particle beam. However, in these systems, there is typically a difficulty in optimizing either the imaging or the beam processing due to physical interference between the imaging and processing subsystems. Often this results in increased working distances for both the imaging and processing subsystems, resulting in loss of spatial resolution for both imaging and processing.

SUMMARY OF THE INVENTION

An object of the present invention is to provide a method for integrating a combined near-infrared and visible light imaging capability into a charged particle beam processing system.

Embodiments of the invention physically separate the imaging subsystem from the charged particle beam processing subsystem, and then transport the substrate to be processed between the imaging and processing regions of the overall system. This may typically require a precision stage to support and transport the substrate. Such stages inevitably have some degree of positional error. This error translates into a potential source of error in the location of the charged particle beam processing location on the substrate, relative to the desired location as determined by the imaging subsystem. Some embodiments of the present invention provide a method for very accurately determining the (open-loop) positioning error, and then for correcting this error (closing the loop) by modifying the substrate position or by deflecting the processing beam.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Figure 1:
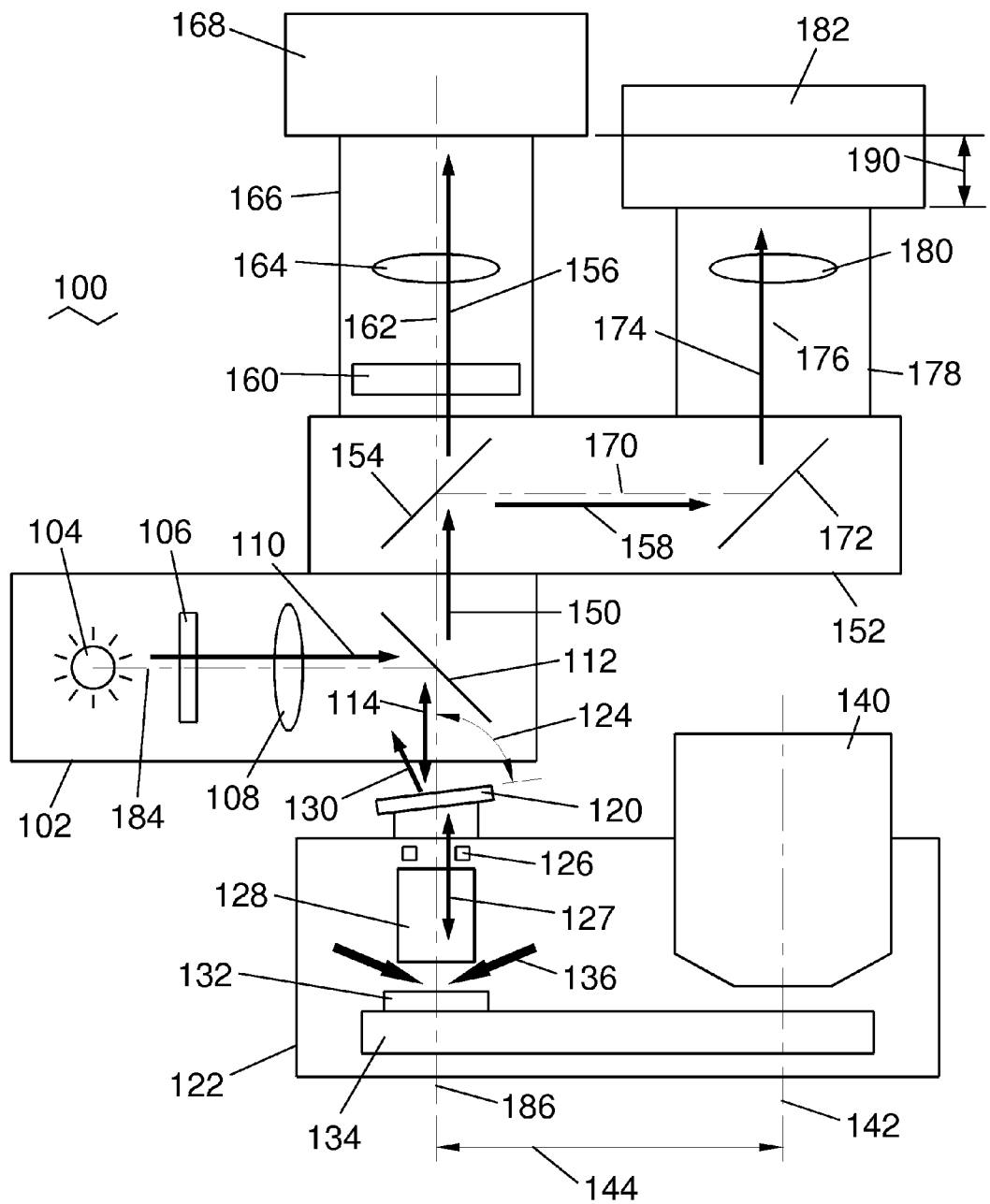
FIG. 1 shows a schematic side cross-sectional view of a first embodiment of the present invention operating in a near-infrared and visible light imaging mode.

Near-infrared (NIR) microscopy is very useful for locating and imaging structures buried by materials that are transparent to NIR wavelengths ($\lambda > 700$ nm), e.g. microcircuitry in silicon. NIR, however, has limited spatial resolution due to its relatively long wavelengths. Visible (VIS) wavelengths are considerably shorter ($700 > \lambda > 400$ nm) and thus a visible wavelength camera may have considerably higher spatial resolution, however, the optical transmissivity of silicon at visible wavelengths is very low. NIR imaging may be used to locate buried structures and VIS imaging may be used for surface features or viewing through relatively thin layers of material (e.g. silicon). Charged particle columns are commonly used for various types of patterned processing of substrates. Focused ion beam columns are used to mill into semiconductor devices to enable the imaging of semiconductor device structures such as metallization, vias, contacts, gates, etc. Electron beam columns, combined with precursor gas feed systems, may perform electron beam-induced etching of substrates or electron beam-induced deposition onto substrates. All of these charged particle columns are comprised in the present invention, with the terminology "CP-columns"

In all imaging optical systems, the size of the focused spot, or the optical resolution, tends to be adversely affected by larger working distances. In order to reduce the working distances, it is typically necessary to position the CP-column very near the substrate surface. This makes it difficult or impossible to achieve small enough working distances for the optical imaging system. Thus, the charged particle processing system of some embodiments of the present invention physically separates the optical imaging system from the charged particle column in order to avoid difficulties in integrating the two systems within a small region. In order to both image and process substrates, a precision stage mechanism is provided for transporting the substrate back-and-forth between the NIR/VIS imaging system and the CP-column. The optical axes of the optical imaging system and the CP-column are thus separated by a distance much larger (e.g., 54 mm) than the scan field of the CP-column or the imaging field of view of the optical system. One difficulty with this separated axis approach is the precise calibration of the locations of the two axes with respect to each other. Such a calibration is necessary in order to locate features optically, and then process these features with the CP-column.

Embodiments of the invention comprise means for imaging at both NIR and VIS wavelengths combined with several types of CP-columns within a charged particle processing system. In some embodiments, imaging at both NIR and VIS may be performed simultaneously using separate NIR and VIS imaging detectors. In other embodiments, a single detector may alternate between NIR and VIS imaging. Multiple types of illuminators are comprised by the invention, along with both normal (bright-field) and grazing incidence (dark-field) illumination systems. This invention includes the uses of a tilted vacuum viewport for use of the microscope in vacuum systems. The tilted viewport eliminates reflections (from top-down bright-field illumination) without the need for anti-reflecting coatings. This is a preferred solution since achieving low reflection with coated optics is difficult due to the wide wavelength requirements (0.3 to >2 microns).

Major Subsystems of the Charged Particle Processing System

All embodiments of the charged particle processing system of the present invention comprise five preferred subsystems, each briefly characterized in the following sections, and in more detail in the descriptions of the four embodiments.

Optical Illumination Subsystem

The optical illumination subsystem provides the source of near-infrared (NIR) and visible (VIS) light to the substrate to be processed. Various possible illumination sources are possible within the present invention, including, but not confined to, the following:

a) A single, broad-spectrum light source, such as a halogen lamp.

b) A dual light source, in which a first source provides mostly NIR radiation, and a second source provides mostly VIS radiation, and in which both light sources operate in parallel.

c) A dual light source, in which a first source provides mostly NIR radiation, and a second source provides mostly VIS radiation, and in which the two light sources operate independently of each other. In this illumination configuration, the optical illumination subsystem at any one time may be providing only NIR light, only VIS light, or a combination of both NIR and VIS light. The relative intensities of the NIR and VIS sources may also be adjusted to compensate for any relative detection sensitivity differences between the NIR and VIS detectors.

Also comprised within the illumination subsystem, may be one or more diffusers, lenses, and beam-splitting mirrors, as discussed in FIGS. 1, 2, and 16-18, below. The illumination subsystem may provide NIR and VIS light through the in-vacuum light optics to enable bright-field imaging. The illumination subsystem may also provide NIR and VIS light to one or more light transmission means used for grazing-incidence surface illumination to enable dark-field imaging. Typically, only bright-field or dark-field imaging may be employed at a time, but rapid alternation between bright-field and dark-field imaging is possible, governed by the speed at which the illumination source location can be changed, as is familiar to those skilled in the art.

Optical Imaging Subsystem

Figure 17:
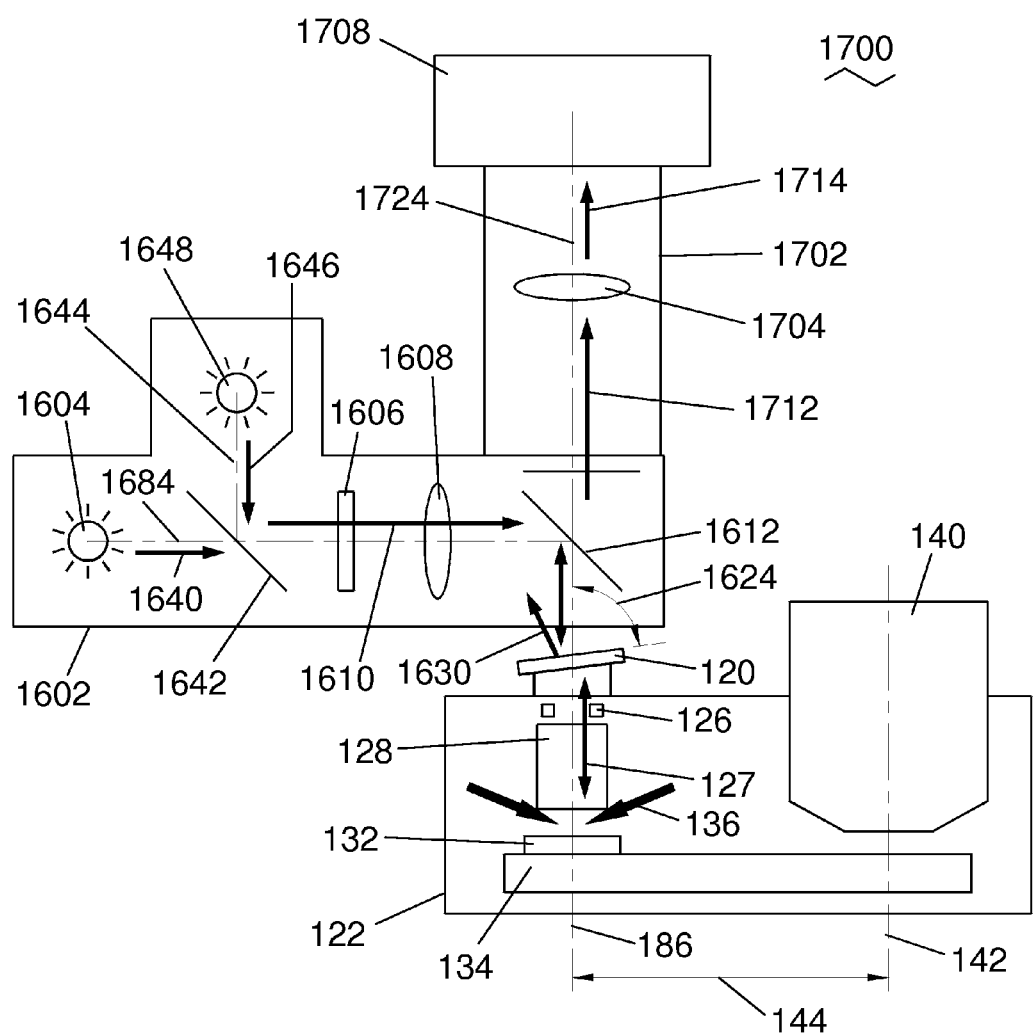
FIG. 17 is a schematic side cross-sectional view of a third embodiment of the present invention.
Figure 18:
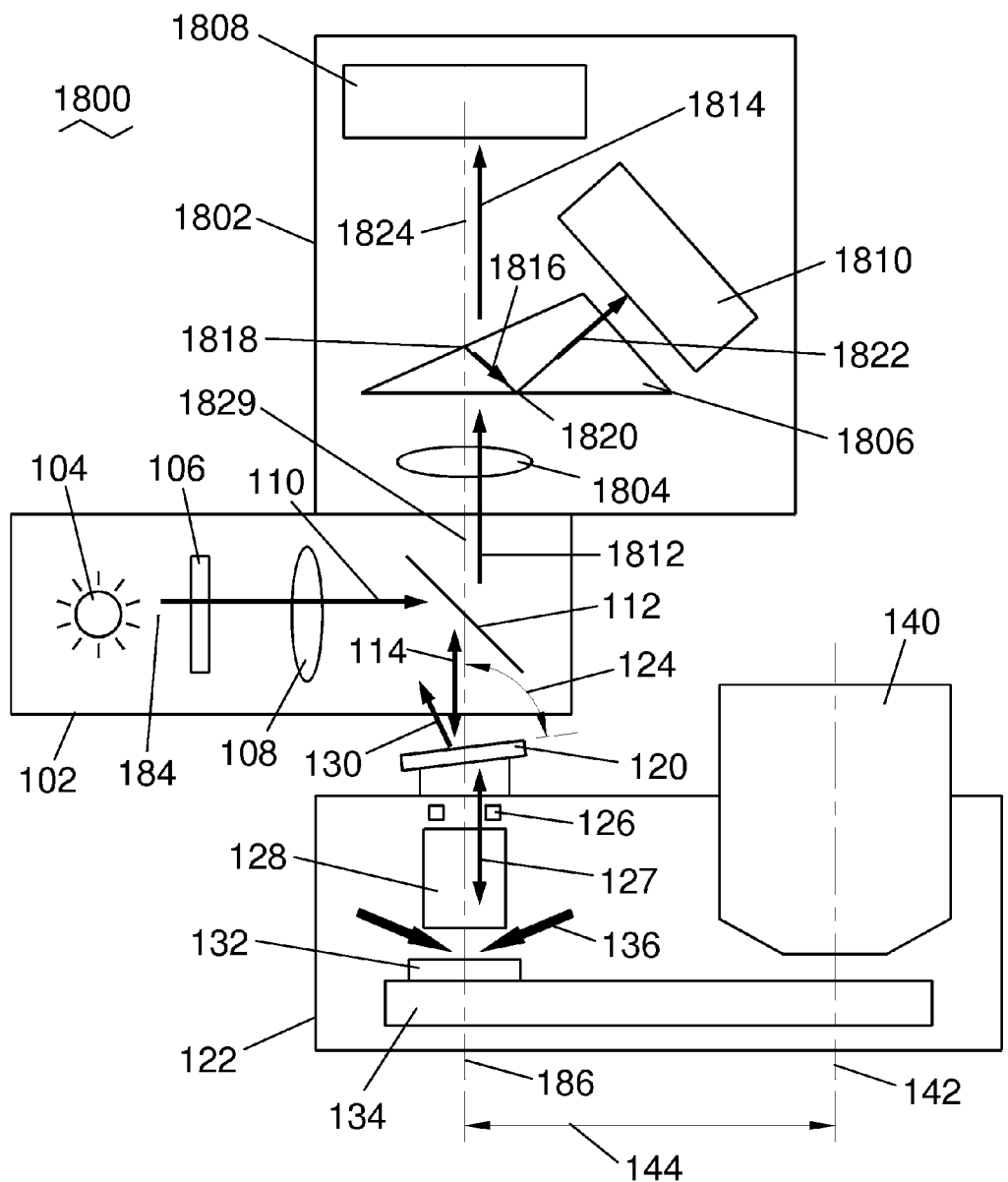
FIG. 18 is a schematic side cross-sectional view of a fourth embodiment of the present invention.

The optical imaging subsystem receives NIR and VIS light transmitted into the air from the in-vacuum light optics through a tilted view port on the main vacuum enclosure. The optical imaging system uses this light from near and at the substrate surface to form images of features within the substrate. These images enable the location and characterization of both pre-existing features on the substrate, as well as the results of processing of the substrate by the CP-column (milling, electron-beam induced etching, electron-beam induced deposition, etc.). While the four embodiments of the present invention described herein comprise three different exemplary optical imaging subsystems, other optical imaging subsystems are possible within the extent of the present invention:

a) Separate NIR and VIS cameras with a beam-splitter for light separation. The first and second embodiments comprise this camera configuration, illustrated in FIGS. 1, 2, and 16, which enables simultaneous acquisition of NIR and VIS images. The light transmitted into the air from the in-vacuum optical subsystem is split by a partially-reflective mirror and transmitted to the two separate cameras. Additional diffusers, lenses, and mirrors may be comprised in these embodiments of the optical imaging subsystem.

b) A single camera with sensitivity for both NIR and VIS light is comprised in the third embodiment of FIG. 17. For this example, a dual light source with independent source controls is preferred, to enable illumination of the substrate with only NIR or only VIS light, thereby allowing images in only the NIR or VIS optical ranges to be acquired. Rapid toggling between the NIR and VIS illumination modes enables alternating NIR and VIS images of the same region on the substrate to be acquired. One advantage of this approach is that very precise overlay of the NIR and VIS images is possible since both images are acquired through the same imaging optics and use the same CCD detector array.

c) A single camera with dual CCD detector arrays, one example being the AD-080 CL multi-spectral camera manufactured by JAI and illustrated in the fourth embodiment of FIG. 18. This camera utilizes two separate CCD arrays, one for NIR and the other for VIS light. Combined NIR and VIS light entering the camera is separated by a prism with dichroic coatings as explained in more detail below. One advantage of this approach is greater simplicity over the dual-camera approach, while maintaining the ability to simultaneously image in both NIR and VIS light. Pixel correlation between the NIR CCD array and the VIS CCD array is within a ¼ pixel.

In-Vacuum Light Optics

The in-vacuum light optics perform two preferred functions:

a) Transmitting NIR and VIS light from the optical illumination subsystem to the substrate surface to enable bright-field imaging.

b) Collecting and transmitting scattered NIR and VIS light from at and near the substrate surface to the tilted view port on the main vacuum enclosure. Further details on the operational and design requirements for the in-vacuum light optics are discussed below for the four embodiments of the present invention described herein.

Charged Particle Column

As discussed above, at least three types of charged-particle columns may be utilized within the scope of the present invention, including focused ion beam columns configured for ion beam milling, electron beam columns configured for electron-beam induced etching, and electron beam columns configured for electron-beam induced deposition. Preferred requirements for all these types of CP-columns are:

a) High or ultra-high vacuum—this is generally provided by a combination of one or more of the following: turbo pumps, cryopumps, diffusion pumps, scroll pumps for rough down and backing of the turbo pumps or diffusion pumps, etc. Pumping systems are well known to those skilled in the art and are not part of the present invention.

b) Electrical feedthroughs—typically required to provide voltages and currents to control various charged particle beam lenses, deflectors, blankers, etc. In some cases, feedthroughs for cooling fluids (liquids or gases) may also be required.

c) For electron-beam induced etch and deposition processes requiring etchant or deposition precursor gases, feedthroughs for these gases may be necessary. Details of the design of the CP-column, pumping systems, and feedthroughs are well known to those skilled in the art.

Main Vacuum Chamber and Precision Stage

The main vacuum chamber contains the in-vacuum light optics, the precision substrate stage, and all or part of the CP-column. Other elements which may be comprised in this subassembly include one or more fiber optics for transmitting NIR and VIS light to the substrate surface as discussed in the optical illumination subsystem, above. Also, a gas-feed subsystem may be provided to enable electron-beam induced etch and deposition processes. The precision stage will typically comprise at least two motion axes and drive mechanisms, as well as positional measurement means such as encoders or laser interferometers. The design of vacuum chambers, precision stages, and CP-columns is familiar to those skilled in the art.

A preferred element of the main vacuum enclosure is the tilted view port through which the NIR and VIS light from the optical illumination subsystem is directed to the substrate surface for bright-field imaging. This view port also enables scattered light collected by the in-vacuum optics to be transmitted out into the air, and hence to the optical imaging subsystem. Details of the design of this view port are discussed in FIG. 1, below.

First Embodiment of the Invention

Figure 2:
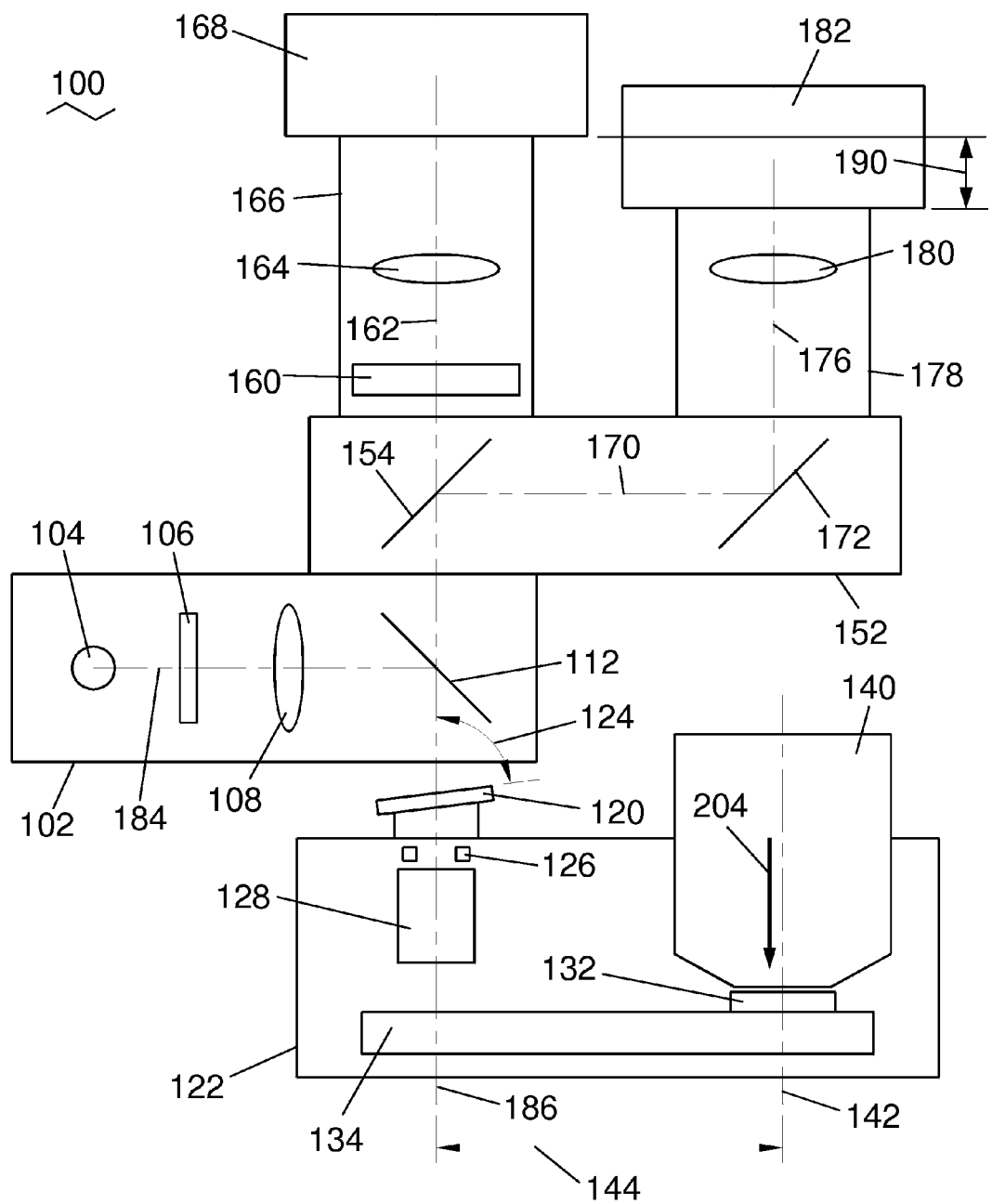
FIG. 2 shows the first embodiment illustrated in FIG. 1 operating in a charged particle beam processing mode.

FIGS. 1 and 2 are schematic side cross-sectional views of a first embodiment 100 of the present invention. In FIG. 1, the first embodiment is illustrated operating in the NIR/VIS imaging mode. In FIG. 2, the first embodiment is shown during processing by the CP-column.

Precision stage 134 is within main vacuum enclosure 122, which also contains the CP-column 140, the objective lens 128, optical shield 126, and substrate 132 supported by stage 134. Illumination 136 strikes the surface of substrate 132 at a glancing angle, enabling dark-field imaging, as discussed in FIG. 15, below. Bi-directional arrow 127 illustrates both the NIR/VIS illumination normally incident on the substrate surface to enable bright-field imaging (the downward arrow), but also the NIR/VIS light traveling upwards from near and at the substrate surface which will be used for imaging. The need to transmit both NIR and VIS light places stringent demands on the objective lens with respect to optical transmissivity over such a wide wavelength range. The purpose of optical shield 126 is to minimize the reflected stray light off the interior walls of the main vacuum enclosure which can pass into the optical imaging subsystem. Shield 126 may be implemented by a rubber o-ring or other light-absorbing ring, or by a light-absorbing coating on all surfaces from which stray light could conceivably scatter into the tilted view port 120. The optical axis 186 of the in-vacuum optics is separated from the optical axis 142 of the CP-column by a distance 144—the methods illustrated in FIGS. 3-13 are used to calibrate distance 144 to less than a micrometer, thereby enabling precise positioning of the charged particle processing beam over the region on the substrate where processing is to be performed. The mechanical design of the main vacuum enclosure, including the mounting for the in-vacuum optics and the CP-column should ensure long-term mechanical stability, including provisions for minimizing thermal expansion, in order to maintain separation distance 144 essentially unchanged (to dimensions <1 μm) over time-scales exceeding the substrate processing times.

The optical illumination subsystem 102 comprises a broad-spectrum single light source 104, which may typically be enclosed by a reflector (not shown) to maximize light collection efficiency. On the axis 184 of the illumination subsystem 102, may be other elements such as an (optional) diffuser 106, a collimating lens 108, and a partially-reflective mirror 112. Bi-directional arrow 114 illustrates the bi-directional nature of the light between the tilted view port 120 and the partially-reflective mirror 112. Light 110 from light source 104 passes through (optional) diffuser 106 and is collimated by lens 108. That portion of light 110 which is reflected by mirror 112 is represented by the downward-directed part of arrow 114, passing on through tilted view port 120 and into the in-vacuum optical subsystem. The scattered light from the substrate which passes back through up tilted view port 120 is represented by the upward-directed part of arrow 114. A portion of the downward-directed light from the optical illumination subsystem is reflected off the outer and inner surfaces of the view port 120, as illustrated by arrow 130. The reason for tilting view port 120 can now be seen—if view port 120 were not tilted (typically with an angle 124 of approximately 83° to the optical axis 162, that is, a normal to the surface is tilted about 7° from the optical axis 110) then reflected light 130 would pass directly into the optical imaging system, combining with the light 127 scattered from the substrate. Since this scattered light 130 is essentially "noise", and contains no information about the substrate, combining light 130 with the upward-directed light 127 will undesirably reduce the signal to noise and contrast in the image.

Light 150 from sample 132 passes through partially-reflective mirror 112, traveling parallel to axis 186 and, enters the optical imaging subsystem comprising: mirror enclosure 152, NIR optical tube 166, NIR camera 168, VIS optical tube 178, and VIS camera 182. Partially-reflective mirror 154 is typically configured to reflect a portion 158 of the NIR and VIS light 150 along axis 170, towards fully-reflective mirror 172. Light 174 which was reflected off mirror 172 passes along axis 176, through lens 180, and into the VIS camera 182. Another portion 156 of NIR and VIS light 150 passes through partially-reflective mirror 154 along axis 162, then through (optional) diffuser 160, lens 164, and into the NIR camera 168. The degree of reflectivity of partially-reflecting mirror 154 may be adjusted to compensate for the relative detection efficiencies of the NIR and VIS cameras, for example a reflection-to-transmission ratio of 80:20 may be employed for typical CCD detector array sensitivities for NIR and VIS light. Due to a number of factors such as the longer path length from partially-reflective mirror 154 to the VIS camera, compared with the NIR camera, as well as other factors, it may be necessary to position the two cameras 168 and 182 at differing heights, as illustrated by arrow 190.

FIG. 2 illustrates the first embodiment from FIG. 1 operating in the charged-particle beam processing mode. The substrate 132 has been moved to the right a distance 144 corresponding to the nominal separation between the light optical axis 186 and the axis 142 of the CP-column 140. Note that the optical source 104 need not be on during this step, however, there is no need to turn source 104 off to perform charged-particle beam processing. Many NIR and VIS light sources may exhibit increased life-times if left on for extended periods, as is familiar to those skilled in the art. The two methods illustrated in FIGS. 3-11 and 12-13 are used compensate for any relative positional errors of the substrate between optical imaging and processing.

First Method for Calibrating the Distance Between the Axis of the Imaging System and the Axis of the Charged Particle Column FIGS. 3-11 illustrate a first method for calibrating the distance 144 between the axis 186 of the in-vacuum optics and the axis 142 of the CP-column as shown in FIGS. 1, 2, and 16-18. An X-Y coordinate system is shown for clarity in FIGS. 3-11, in which the X-axis 381 is the primary travel direction for precision stage 134 for all four embodiments. The Y-axis 382 represents a small offset between the optical axes 186 and 142 perpendicular to the primary travel axis 304 of the stage 134.

Figure 3:
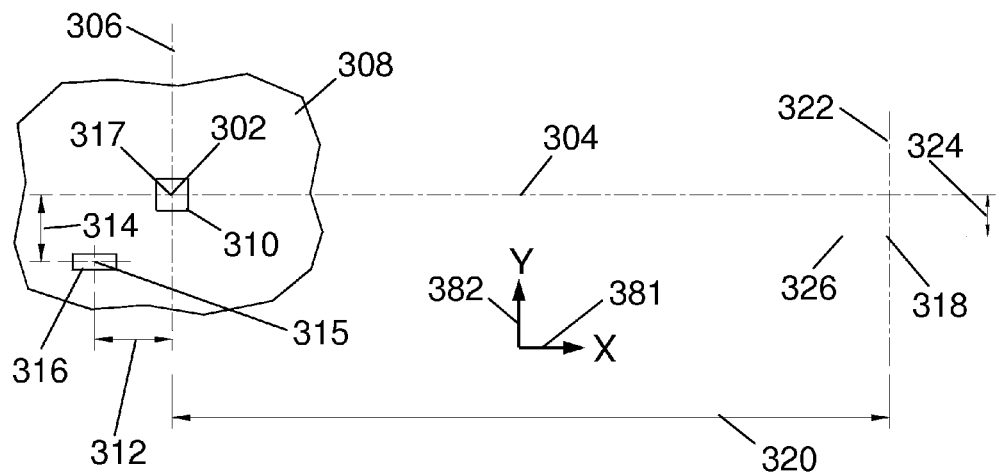
FIG. 3 shows a schematic representation of the first step in a procedure for calibrating the offset between the axis of the in-vacuum optics and the axis of the charged-particle column, wherein an expendable feature is imaged using near-infrared or visible light.

FIG. 3 shows the first step in the method—the use of NIR and VIS imaging to optically locate a feature on the substrate which would be undetectable using the charged particle beam generated by the CP-column—these features will be termed "CP-invisible" hereinafter. There are two types of CP-invisible features on the substrate portion 308 (corresponding to part of substrate 132 in FIGS. 1, 2, and 16-18):

a) "Expendable"—these are features on the substrate which are not of functional significance. These features have a known location relative to the "Critical" features through the computer-aided design (CAD) patterning data.

b) "Critical"—charged particle beam processing is desired at the locations of "critical" features. Such processing might typically be focused ion beam (FIB) milling down through layers of the device structure (such as metal interconnects) for imaging of layer defects or for circuit editing, or deposition of an extra metal connection for circuit editing.

Figure 4:
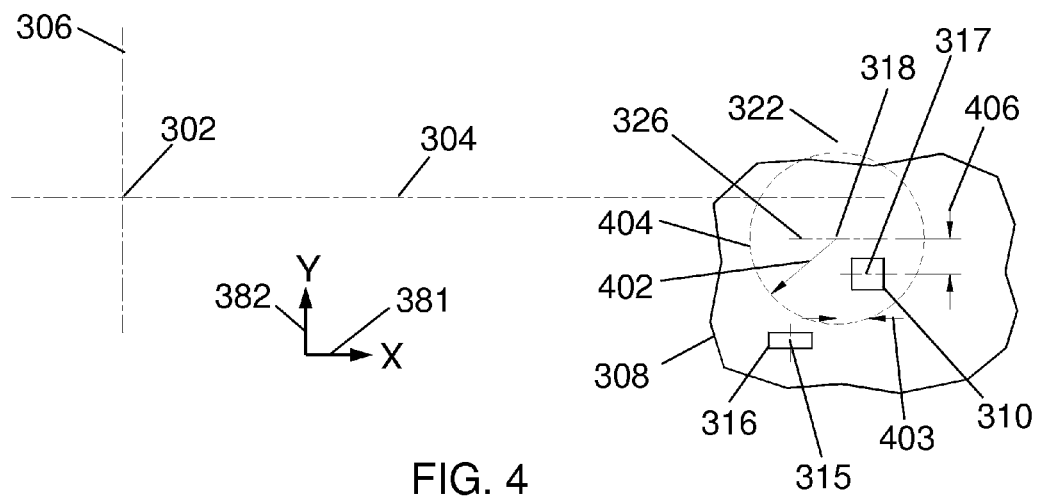
FIG. 4 shows a schematic representation of the second step in the procedure of FIG. 3, wherein a substrate is moved under the charged particle column.

The in-vacuum optics has an axis 302 (corresponding to axis 186 in FIGS. 1, 2, and 16-18), at the left of FIGS. 3-11, while the CP-column 140 has an axis 318 (corresponding to axis 142 in FIGS. 1, 2, and 16-18) at the right of FIGS. 3-11. The primary travel axis for precision stage 134 is axis 304 (along the X-direction). Axis 326 (along the X-direction) and axis 322 (along the Y-direction) intersect the axis 318 of the CP-column 140. Similarly, axis 304 (along the X-direction) and axis 306 (along the Y-direction) intersect axis 302 of the in-vacuum optics. The X-offset 320 and the Y-offset 324 between axes 302 and 318 may be determined to sub-micron accuracy by the method illustrated in FIGS. 3-11. The center 317 of an expendable CP-invisible feature 310 is positioned using stage 134 on axis 302. Offset to the lower left of expendable feature 310 is critical feature 316, having a center 315 which is offset along the X-direction a distance 312, and offset along the Y-direction a distance 314 from the center of expendable feature 310—both these offsets are known a priori from the CAD database. After feature 310 has been positioned on the axis 302 of the in-vacuum optics, the precision stage 134 then moves the substrate portion 308 (along with the entire substrate 132) over to a location under the CP-column 140, as shown in FIG. 4.

In FIG. 4, the substrate portion 308 has been moved to the approximate location of the axis 318 of the CP-column 140. This positioning process has a predicted error 404 illustrated by the circle of radius 402 centered on axis 318. If the exact offsets 304 and 324 between axes 302 and 318 were knowable a priori, then the method shown in FIGS. 3-11 would be unnecessary. However, due to mechanical inaccuracies, and the extremely precise positioning requirements for charged particle beam processing, it is typically necessary to calibrate the offset 144 between column axes 186 and 142 in FIGS. 1, 2, and 16-18. Due to stage inaccuracies, the center 317 of expendable feature 310 has an X-offset 403 and a Y-offset 406, relative to axis 318. Note that critical feature 315 in FIG. 4 has the same offset relative to expendable feature 310 as in FIG. 3, as is expected.

Figure 5:
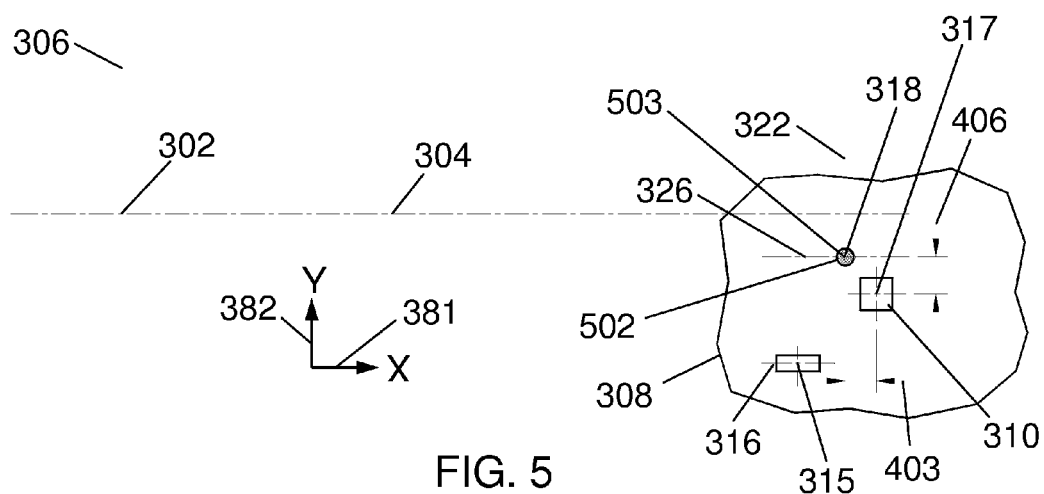
FIG. 5 shows a schematic representation of the third step in the procedure of FIGS. 3-4, wherein a feature has been created on the substrate surface by the charged particle column.

Now, in FIG. 5, the CP-column 140 performs a processing operation (milling, etch, deposition, etc.) to produce a light optically-detectable feature 502, with a center 503 coincident with the axis 318 of the CP-column 140. Note that it is important that feature 502 does not end up on top of the critical feature 316—avoiding this situation may require that the offset between features 310 and 315 meets this requirement:

$$\text{Offset (features 310 to 315)} = \sqrt{[(X\text{-offset 312})^2 + (Y\text{-offset 314})^2]} > (\text{radius 402}),$$

where the X-offset 312 and Y-offset 314 are derived from the CAD patterning data of the substrate. Where there is more than one critical feature, it may be necessary to find an expendable feature 310 which meets this criterion for all critical features simultaneously.

Figure 6:
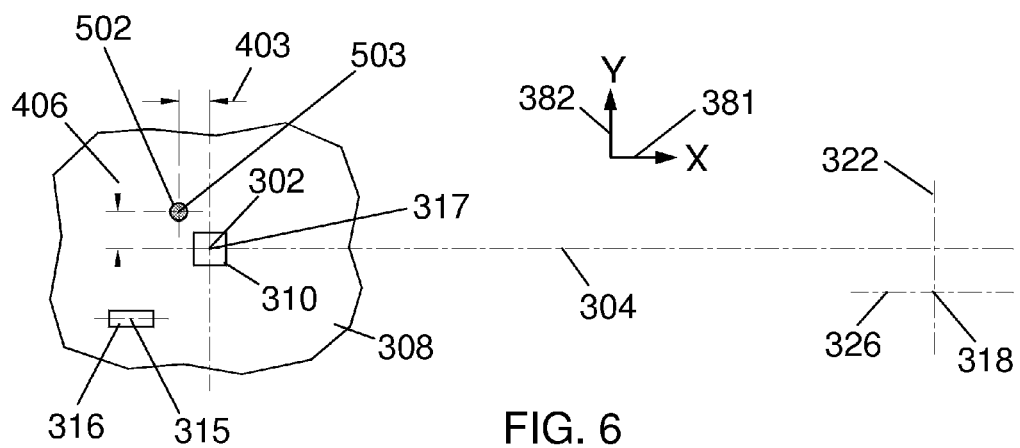
FIG. 6 shows a schematic representation of the fourth step in the procedure of FIGS. 3-5, wherein the feature created in FIG. 5 is located by near-infrared and visible light imaging.

After the optically-visible feature 502 has been created by CP-column 140, the substrate portion 308 is moved by precision stage 134 back to a location under the in-vacuum optics, as illustrated in FIG. 6. The center 317 of expendable feature 310 is again positioned on axis 302 of the in-vacuum optics, as in FIG. 3, however, now the new feature 502 is visible with NIR, VIS, or both NIR and VIS imaging. Note that this requires that the radius 402 of the error circle 404 in FIG. 4 must be smaller than the field of view of the in-vacuum optics—this should be the case for any well-designed light optical system. Now, the X-offset 403 and the Y-offset 406 of feature 502 relative to axis 302 may be determined precisely, using the (known) magnification of the light optics. Offsets 403 and 406 are then recorded either manually or automatically by the system controller.

Figure 7:
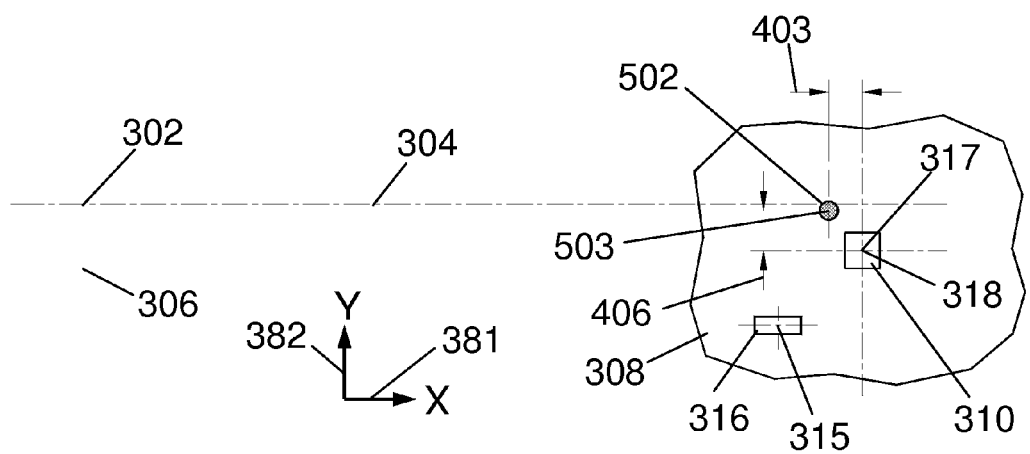
FIG. 7 shows a schematic representation of the fifth step in the procedure of FIGS. 3-6, wherein the substrate is positioned under the charged particle beam for the creation of a second feature.

FIG. 7 shows the substrate portion 308 has been moved back to the CP-column 140, but now with a position corrected by offsets 403 and 406. Thus, the center 317 of expendable feature 310 is now located much closer to the axis 318 of the CP-column 140, as shown. A second charged particle beam processing operation is now performed, similar or identical to that in FIG. 5.

Figure 8:
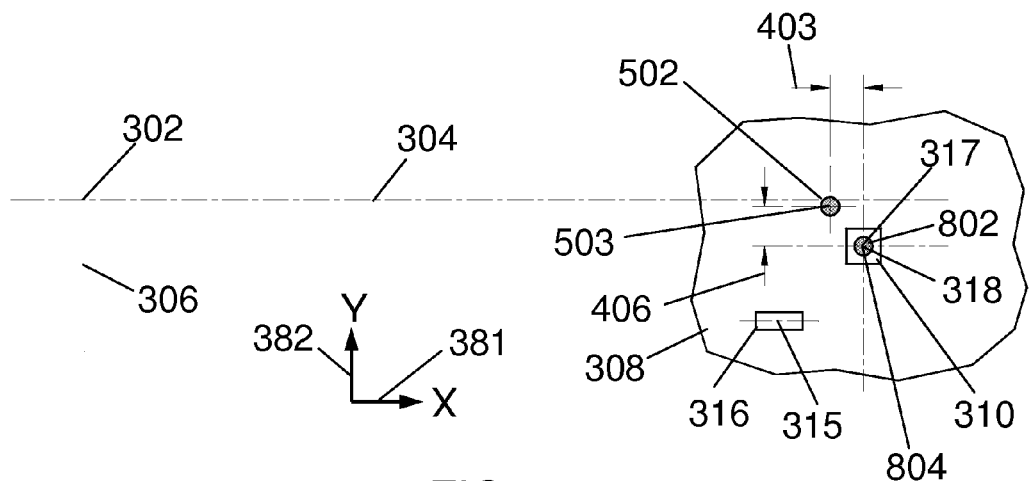
FIG. 8 shows a schematic representation of the sixth step in the procedure of FIGS. 3-7, wherein the charged particle column has created a feature directly above an expendable feature on the substrate.

FIG. 8 shows the results of this second processing operation—a feature 802 has been created on the substrate portion 308, where the center 804 of the new feature 802 is coincident with the center 317 of expendable feature 310, and also coincident with the axis 318 of the CP-column 140. Note, however, since expendable feature 310 is CP-invisible, the step shown in FIG. 9 is necessary to confirm that feature 802 is centered on expendable feature 310.

Figure 9:
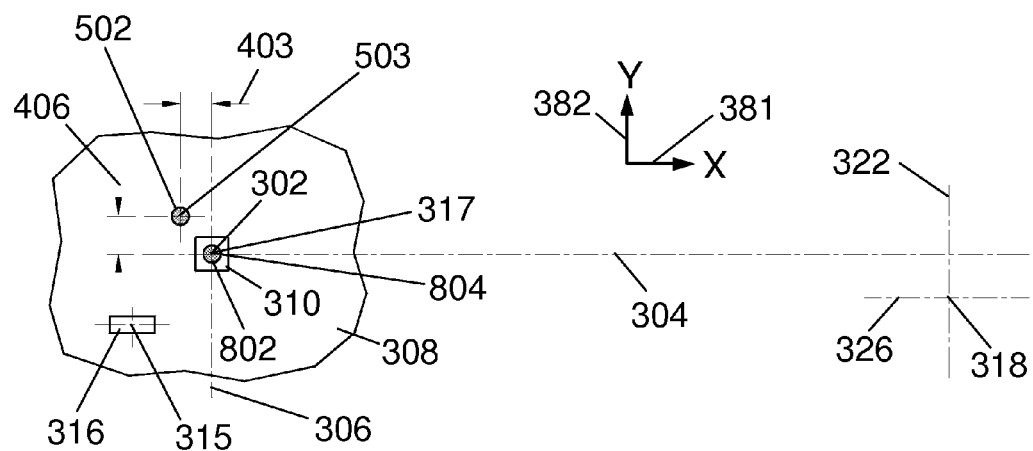
FIG. 9 shows a schematic representation of the seventh step in the procedure of FIGS. 3-8, wherein the second feature created in FIG. 8 is located by near-infrared and visible light imaging.

The substrate portion 308 is moved back under the in-vacuum optics in FIG. 9. As shown, the new feature 802 can be seen using NIR, VIS or both NIR and VIS imaging to be located directly above the expendable feature 310.

Figure 10:
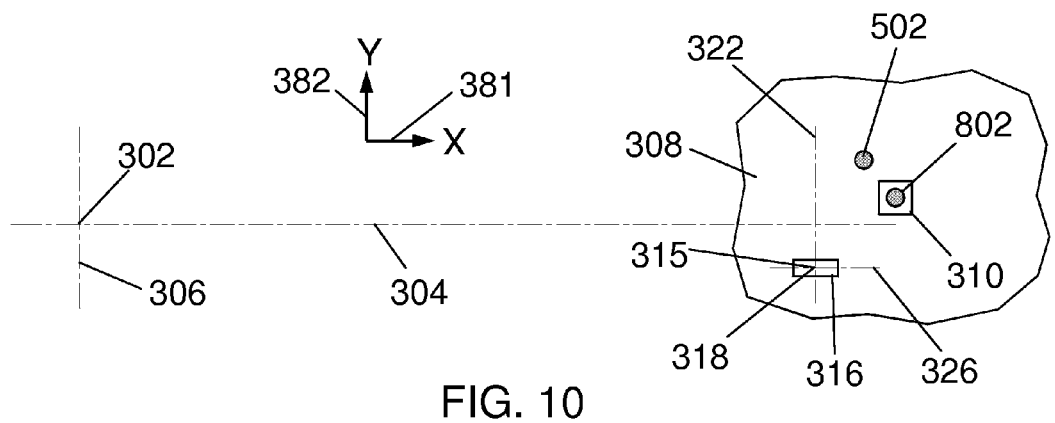
FIG. 10 shows a schematic representation of the eighth step in the procedure of FIGS. 3-9, wherein a critical feature is positioned for charged particle processing.
Figure 11:
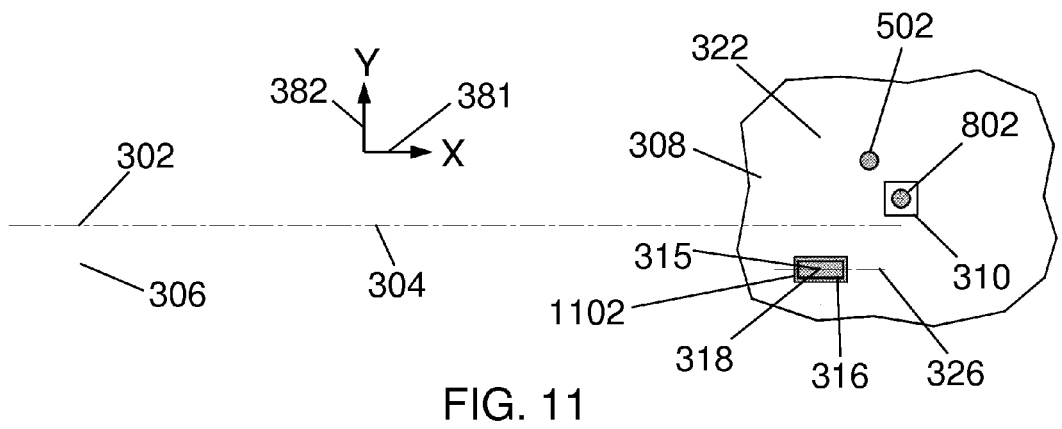
FIG. 11 shows a schematic representation of the last step in the procedure of FIGS. 3-10, wherein the charged particle column has processed the substrate directly at the location of a critical feature.

Now, in FIG. 10, actual charged-particle processing of the substrate portion 308 begins. The portion 308 of substrate 132 has been moved by the precision stage 134 to again position the substrate portion 308 under the CP-column 140. By using the X-offset 403 and the Y-offset 406, combined with the X-offset 312 and Y-offset 314 between expendable feature 310 and critical feature 316, the center 315 of critical CP-invisible feature 316 has been positioned on the axis 318 of the CP-column 140. Finally, FIG. 11 illustrates a feature 1102, created by the CP-column 140, exactly above the CP-invisible critical feature 316, as desired.

Second Method for Calibrating the Distance Between the Axis of the Imaging System and the Axis of the Charged Particle Column The first method for calibrating the inter-column distance shown in FIGS. 3-11 employs only a single expendable CP-invisible feature 310 in order to precisely calibrate the X-Y offsets between the in-vacuum optics and the CP-column. In some cases, particularly where extremely precise positioning of the charged-particle processing beam is required, it may be necessary to utilize a second method in which multiple expendable CP-invisible features are used, as illustrated in FIGS. 12-13.

Figure 12:
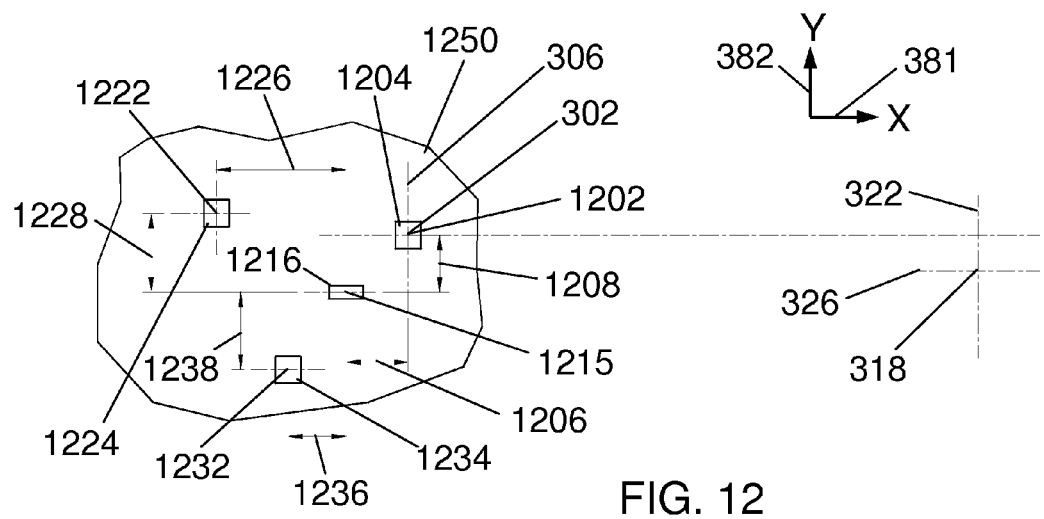
FIG. 12 shows a schematic representation of the first step in an alternative procedure to that shown in FIGS. 3-11 for calibrating the offset between the axis of the in-vacuum optics and the axis of the charged-particle column, wherein a multiplicity of expendable features are imaged using near-infrared or visible light.

FIG. 12 corresponds to FIG. 3 of the first method. Three expendable CP-invisible features 1204, 1224, and 1234, with respective centers 1202, 1222, and 1232 are first imaged optically, using NIR, VIS, or both NIR and VIS imaging. A critical feature 1216 with center 1215 is located within a triangle formed by the three expendable features 1204, 1224, and 1234. Expendable feature 1204 has X-offset 1206 and Y-offset 1208 relative to critical feature 1216. Similarly, expendable feature 1224 has X-offset 1226 and Y-offset 1228 relative to critical feature 1216, and expendable feature 1234 has X-offset 1236 and Y-offset 1238 relative to critical feature 1216. All offsets 1206, 1208, 1226, 1228, 1236, and 1238 are known from the CAD patterning data.

Figure 13:
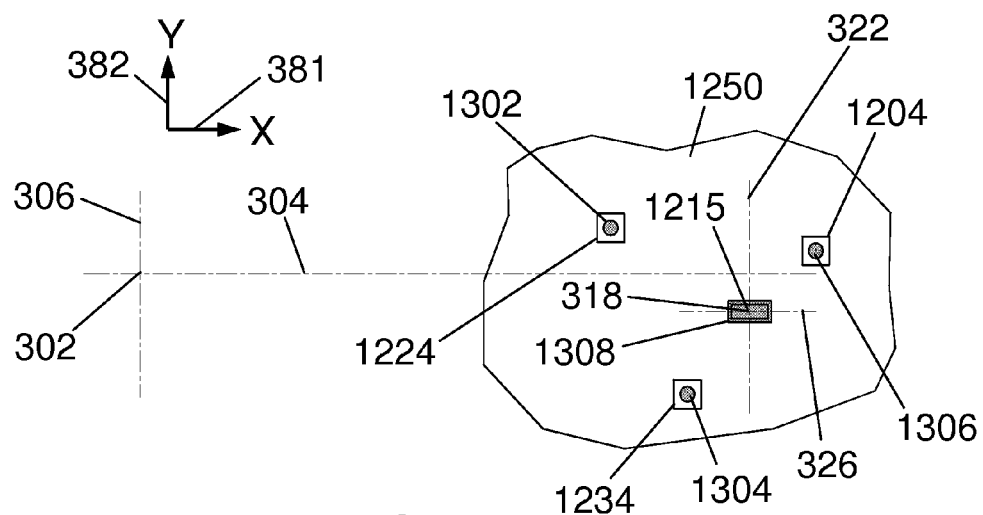
FIG. 13 shows a schematic representation of the final step in the alternative beam calibration procedure of FIG. 12.

Three charged-particle processing steps then create three features 1306, 1302, and 1304, centered on the expendable CP-invisible features 1204, 1224, and 1234, respectively, as shown in FIG. 13—this step is comparable to that shown in FIG. 8. Finally, using triangulation between the three marks 1306, 1302, and 1304, more precise positioning of critical CP-invisible feature 1216 may be possible. A final charged particle processing step is performed to create feature 1308 above critical feature 1216.

Comparison of Bright-Field and Dark-Field Illumination

Figure 14:
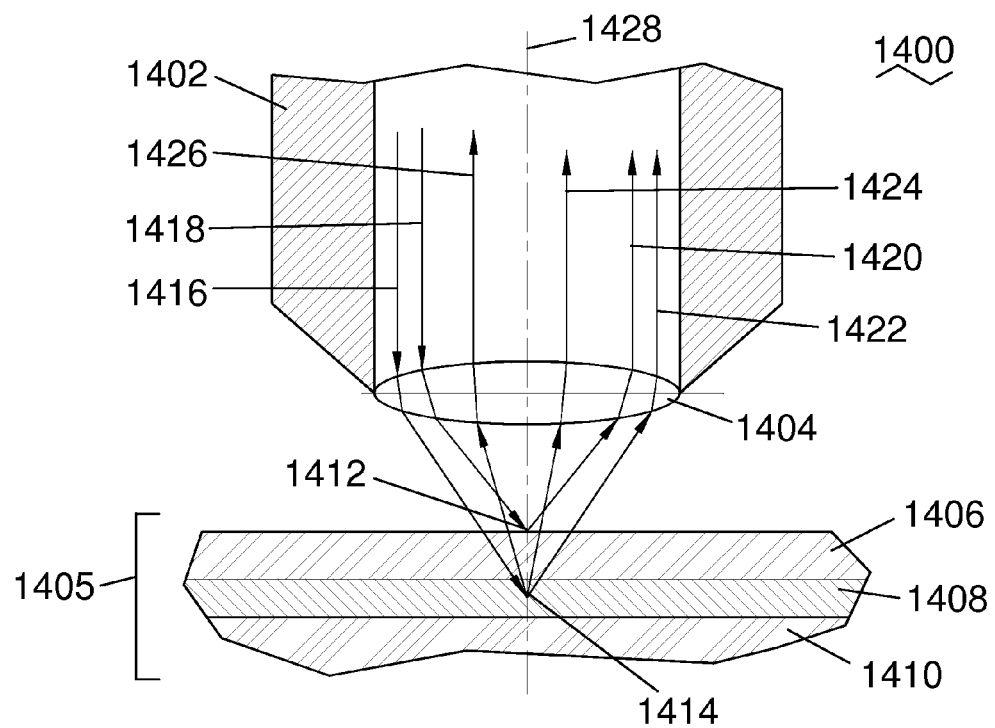
FIG. 14 illustrates illumination in a bright-field imaging mode that can be used with embodiments of the invention.

As illustrated in FIGS. 1, 2, and 16-18, two complementary illumination modes are possible in all embodiments of the charged particle processing system of the present invention. FIG. 14 illustrates bright-field imaging mode. Arrow 1418 represents NIR and VIS illumination which passes down through the objective lens 128 of the in-vacuum optics and is reflected off the surface of substrate 1405 at point 1412. Arrow 1416 represents NIR and VIS illumination which passes down through the objective lens 128 of the in-vacuum optics and penetrates into the substrate 1405, scattering off expendable and critical features within device layer 1408 at point 1414. The lower end 1402 of the objective lens 128 contains an imaging lens 1404 which directs the NIR and VIS illumination towards a small area of the substrate 1405 containing points 1412 and 1414. Especially for NIR light, for which silicon is relatively transparent at $\lambda > 1.1$ μm (photon energies below the band gap), a substantial portion of the illumination will penetrate into the various layers 1406, 1408 and 1410 of the substrate 1405, for example to a point 1414 within device layer 1408. Layer 1406 is a surface coating above a device layer containing both expendable and critical features, and layer 1410 represents the bulk silicon wafer on which the circuits are fabricated.

NIR and VIS light 1420 reflecting off the surface of substrate 1405 at point 1412 contains no useful information about features within the device layer 1408, and thus represents an unwanted background signal which, in bright-field mode, is added to the desired signal 1422 arising from photons scattered out of the device layer 1408 at point 1414. Thus, bright-field imaging may have a reduced contrast and signal-to-noise due to the ability of reflected light off the substrate surface to enter lens 1404 of the in-vacuum optics.

Figure 15:
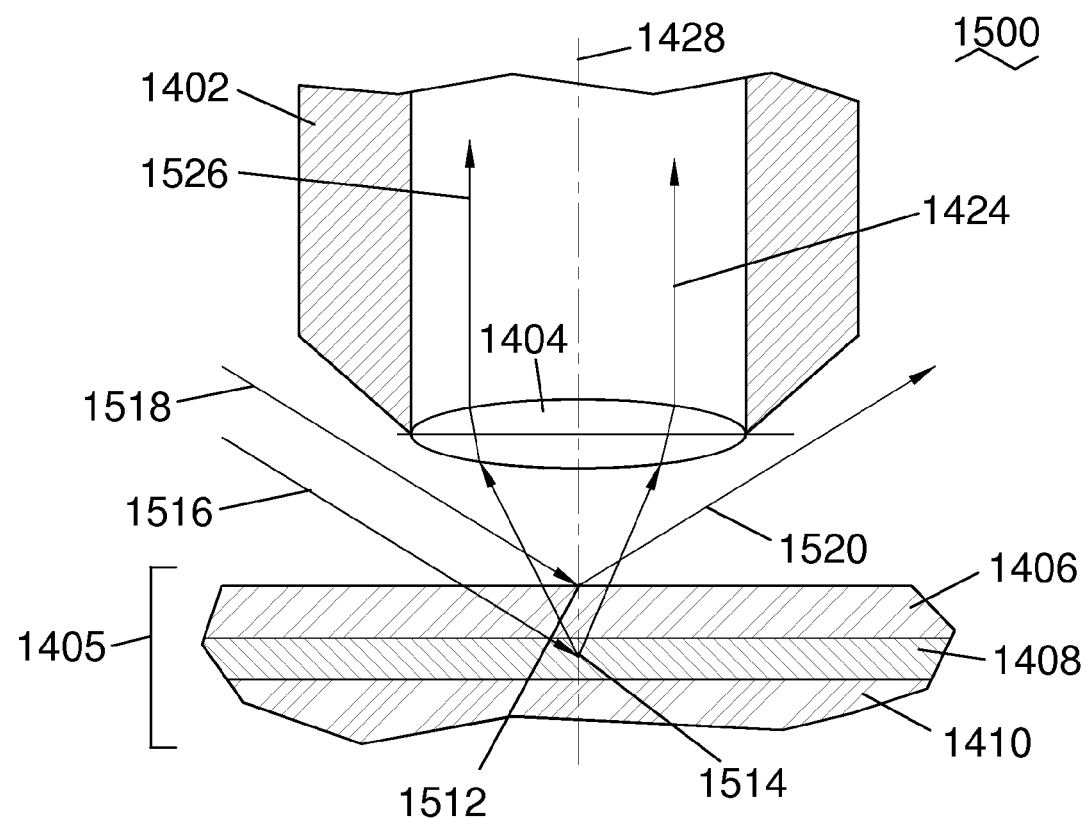
FIG. 15 illustrates illumination in a dark-field imaging mode that can be used with embodiments of the invention.

FIG. 15 illustrates illumination in dark-field imaging mode 1500. Arrow 1518 represents NIR and VIS illumination which is directed towards the substrate 1405 at a glancing angle as shown, and then reflected off the surface of substrate 1405 at point 1512. Arrow 1516 represents NIR and VIS illumination which penetrates into the substrate 1405, scattering off expendable and critical features within device layer 1408 at point 1514. Comparison of FIGS. 14 and 15 shows that for dark-field illumination, any NIR or VIS illumination which reflects off the surface at point 1512 does not enter lens 1404, and thus does reduce contrast or signal-to-noise. The NIR and VIS light which scatters from within the substrate 1405 is collected in the same way as for bright-field mode in FIG. 14.

Second Embodiment of the Invention

Figure 16:
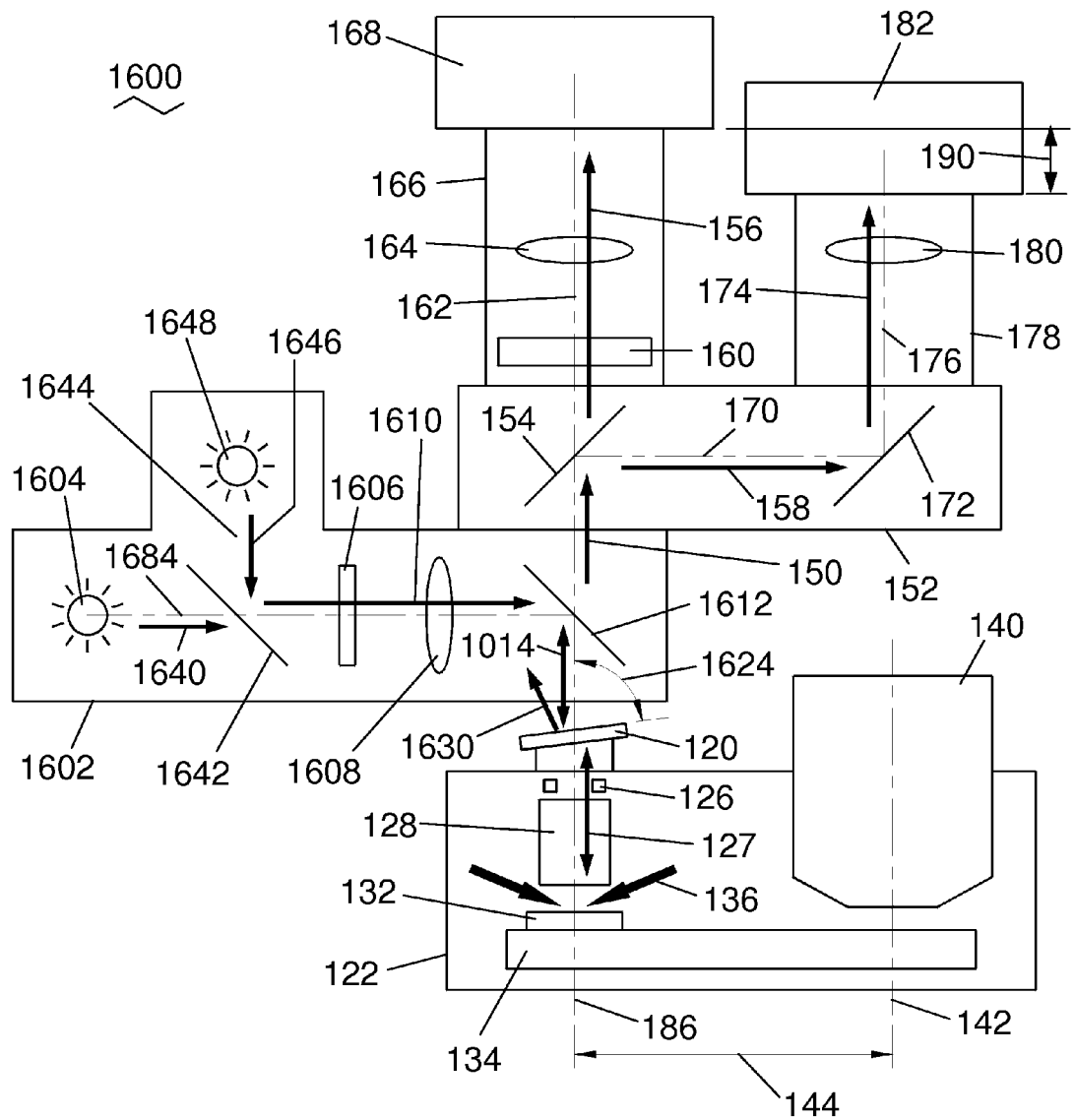
FIG. 16 is a schematic side cross-sectional view of a second embodiment of the present invention.

FIG. 16 is a schematic side cross-sectional view of a second embodiment 1600 of the present invention, in which the CP-column 140, optical imaging subsystem (comprising: mirror enclosure 152, NIR optical tube 166, NIR camera 168, VIS optical tube 178, and VIS camera 182), the main vacuum enclosure 122, precision stage 134, and the in-vacuum optics 128 are all the same as for FIG. 1, above. The preferred change from the first embodiment discussed in FIGS. 1 and 2, is the optical illumination subsystem 1602.

Optical illumination subsystem 1602 employs dual light sources, one source 1604 optimized for NIR emission, and the other source 1648 optimized for VIS emission. Either of the two operating modes for the two sources which were discussed above is applicable to this embodiment—i.e., NIR source 1604 and VIS source 1648 may be configured to operate either simultaneously, or may be configured to be independently-controllable. Both sources 1604 and 1648 may typically be enclosed by reflectors (not shown) to maximize their respective light collection efficiencies. NIR light 1640 from NIR source 1604 passes along axis 1684, and a portion of light 1640 passes through partially-reflective minor 1642. VIS light 1646 from VIS source 1648 passes along axis 1644, and a portion of light 1646 is reflected off partially-reflective minor 1642. Both the NIR light which passes through mirror 1642, and the VIS light which is reflected off mirror 1642 pass along axis 1684, forming light beam 1610, which may pass through an (optional) diffuser 1606, and a collimating lens 1608. A portion of light beam 1610 reflects downwards off partially-reflective minor 1612, forming the downward portion of bi-directional light beam 1014, corresponding to bi-directional arrow 114 in FIG. 1. The same considerations apply to the angle between the inner and outer surfaces of view port 120 for the second embodiment in FIG. 16, as applied to the first embodiment in FIG. 1—it is necessary to ensure that reflected light 1630 off the front and back surfaces of view port 120 cannot pass into the optical imaging subsystem. Scattered light from the substrate which is collected by the in-vacuum optics 128, is partially transmitted through the view port 120 and the partially-reflective mirror 1612, and then into the optical imaging subsystem, corresponding to arrow 150 along axis 162.

Third Embodiment of the Invention

FIG. 17 is a schematic side cross-sectional view of a third embodiment 1700 of the present invention, employing the same optical illumination system as the second embodiment illustrated in FIG. 16, but with a single camera embodying a broad-spectrum detector, capable of both NIR and VIS imaging. All other aspects of the system as the same as for the second embodiment.

Light 1712 which passes through partially-reflective minor 1612 parallel to axis 1724 enters the optical imaging subsystem comprising a light tube 1702, collimating lens (which must transmit both NIR and VIS light) 1704, and a broad-spectrum camera 1708. To obtain NIR images, only NIR source 1604 would be turned on, and VIS source 1648 would be turned off, thus requiring the third configuration for the optical illumination subsystem which was discussed above. Conversely, to obtain VIS images, only VIS source 1648 would be turned on, and NIR source 1604 would be turned off. Clearly, if the two sources 1604 and 1648 are on at the same time, a composite (and probably undesirable) NIR+VIS image would be obtained. If both sources 1604 and 1648 can be turned on and off rapidly, then it will be possible to toggle between NIR and VIS imaging modes rapidly using this embodiment. The relative illumination intensities of the NIR source 1604 and the VIS source 1648 may be adjusted to compensate for sensitivity differences between NIR and VIS light in the detector array (not shown) of broad-spectrum camera 1708.

Fourth Embodiment of the Invention

FIG. 18 is a schematic side cross-sectional view of a fourth embodiment 1800 of the present invention, in which the optical imaging system in FIGS. 1 and 2 comprising dual cameras has been replaced by a single camera assembly 1802 comprising dual CCD detector arrays 1808 (for VIS light) and 1810 (for NIR light) and a beam-splitting prism 1806. As discussed above, one example of this type of camera is the model AD-080 CL multi-spectral camera manufactured by JAI.

Light 1812 which passes through partially-reflective mirror 112 parallel to axis 1829 enters the optical imaging subsystem, passing through entrance lens 1804. The majority of the VIS light passes through the dichroic layer at point 1818 on the prism 1806, forming VIS light beam 1814 traveling along axis 1824 and into VIS light CCD array 1808. Note that due to refraction by prism 1806, axes 1829 and 1824 will not be parallel. The majority of the NIR light reflects off the dichroic layer at point 1818, forming specularly reflected beam 1816, which travels across the width of prism 1806. Beam 1816 then specularly reflects at point 1820, forming reflected beam 1822 which is approximately normally-incident on the side of prism 1806 nearest to NIR CCD array 1810. Thus, two simultaneous images may be acquired—each from one of the two CCD detector arrays operating in parallel within the multi-spectral camera.

As describes above, the various illumination and imaging systems described above can be combined. For example, a single broad-spectrum source and the dual-source, coupled operation illumination system can both be used with a dual camera having a beam splitter or with a single camera assembly having dual integrated detectors. The dual-source, independent operation illumination system can be used with a dual camera having a beam splitter or with a single camera assembly, either a broad spectrum camera or a camera having integrated dual detectors.

While embodiments above use near-infrared radiation, the invention is not limited to near-infrared, although skilled persons will recognize that as the wavelength increases, the resolution decreases and so a shorter wavelength is preferred.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A charged particle beam system for processing a substrate, comprising:
   a charged particle column configured to produce a beam of charged particles which can be focused on the surface of the substrate in a vacuum chamber;
   an in-vacuum optical subsystem positioned inside the vacuum chamber, the optical subsystem configured to collect scattered infrared radiation and visible light from the surface and regions near the surface of the substrate;
   an illumination subsystem positioned outside the vacuum chamber configured to provide infrared radiation and visible light to the surface of the substrate;
   an imaging subsystem, configured to focus the scattered infrared radiation and visible light collected by the in-vacuum optical subsystem onto one or more detectors positioned outside the vacuum chamber; and
   a vacuum viewport to provide an optical path between the inside of the vacuum chamber and the outside of the vacuum chamber, the vacuum viewport including a transparent element that is tilted with respect to the optical path of the light from the illumination system to reduce the amount of reflected radiation entering at least one of the detectors.

2. The charged particle beam system of claim 1, wherein:
   the illumination subsystem is configured to provide near-infrared radiation and visible light to the surface of the substrate;
   the in-vacuum optical subsystem is configured to collect scattered near-infrared radiation and visible light from the surface and regions near the surface of the substrate; and
   the imaging subsystem is configured to focus the scattered near-infrared radiation and visible light collected by the in-vacuum optical subsystem onto one or more detectors.

3. The charged particle beam system of claim 1, wherein the charged particle column is a focused ion beam column, and wherein the processing of the substrate is focused ion beam milling.

4. The charged particle beam system of claim 1, wherein the charged particle column is an electron beam column.

5. The charged particle beam system of claim 4, further comprising a gas feed assembly, configured to provide an etchant gas to the vicinity of the intersection of the electron beam with the substrate, and wherein the processing of the substrate is electron beam induced etching.

6. The charged particle beam system of claim 4, further comprising a gas feed assembly, configured to provide a deposition precursor gas to the vicinity of the intersection of the electron beam with the substrate, and wherein the processing of the substrate is electron beam induced deposition.

7. The charged particle beam system of claim 1, wherein the illumination subsystem comprises a single light source, configured to provide both infrared radiation and visible light.

8. The charged particle beam system of claim 1, wherein the illumination subsystem comprises:
   a first light source configured to provide principally infrared radiation; a second light source configured to provide principally visible light radiation; and optics for combining the radiation from the first and second light sources into a parallel beam.

9. The charged particle beam system of claim 1, further comprising optics for directing the infrared radiation and visible light from the illumination subsystem at a glancing angle to the surface of the substrate for enabling dark-field imaging of the substrate.

10. The charged particle beam system of claim 1, further comprising optics for directing the infrared radiation and visible light from the illumination down through the in-vacuum optical subsystem at approximately normal incidence to the surface of the substrate for enabling bright-field imaging of the substrate.

11. The charged particle beam system of claim 1 in which the imaging subsystem comprises a broad spectrum camera having a single detector that can form an image using infrared radiation or visible light.

12. The charged particle beam system of claim 1 in which the imaging subsystem comprises a single camera having two detector, one that can form an image using infrared radiation and one that can form an image using visible light.

13. The charged particle beam system of claim 12, wherein the imaging subsystem further comprises a partially reflective mirror that divides incoming light into two parts, each part containing both infrared and visible light, with one part directed at the detector that can form an image using infrared radiation and the other part directed at the detector that can form an image using visible light.

14. The charged particle beam system of claim 1 in which the imaging subsystem comprises a first camera for forming an image using scattered infrared radiation and a second camera for forming an image using visible light.

15. The charged particle beam system of claim 14, wherein the imaging subsystem further comprises a partially reflective mirror that divides incoming light into two parts, each part containing both infrared and visible light, with one part directed at said first camera and the other part directed at said second camera.

16. The calibration subsystem of claim 1, further comprising:
- an expendable feature on the substrate initially located under the imaging subsystem;
- a precision stage configured to transport the substrate alternately between a location under the imaging subsystem and a location under the charged particle column;
- a first structure on the substrate under the charged particle column formed using charged particle beam processing; and
- a second structure on the substrate under the charged particular column formed using charged particle beam processing, wherein said second structure is located by
- transporting the substrate back to a location under the imaging subsystem, where the transport distance is exactly opposite to the expected offset between the imaging subsystem and the charged particle column;
- imaging said first structure and determining the offset of said first structure with respect to said expendable feature, wherein the offset corresponds to the difference between the actual and the expected offset between the imaging subsystem and the charged particle column; and
- transporting the substrate to a location under the charged particle column, wherein the transport distance is calibrated using said offset.

* * * * *